United States Patent
Young et al.

(10) Patent No.: US 6,297,506 B1
(45) Date of Patent: Oct. 2, 2001

(54) SYSTEM AND METHOD FOR REDUCING PILE-UP ERRORS IN MULTI-CRYSTAL GAMMA RAY DETECTOR APPLICATIONS

(76) Inventors: John W. Young, 709 Gulfwood Rd., Knoxville, TN (US) 37923; J. Clifton Moyers, 117 Clifton Cir., Oak Ridge, TN (US) 37830

(*) Notice: Subject to any disclaimer, the term of this patent is extended or adjusted under 35 U.S.C. 154(b) by 0 days.

(21) Appl. No.: 09/533,714

(22) Filed: Mar. 23, 2000

(51) Int. Cl.⁷ .................................................. G01T 1/208
(52) U.S. Cl. .............................................................. 250/369
(58) Field of Search .................................... 250/369, 362, 250/366, 367, 363.07

(56) References Cited

U.S. PATENT DOCUMENTS

| | | |
|---|---|---|
| 2,910,592 | 10/1959 | Armistead . |
| 3,432,660 | 3/1969 | Anger . |
| 3,752,988 * | 8/1973 | Culver ................................ 250/269.6 |
| 4,186,307 * | 1/1980 | Tanaka et al. ................... 250/363.02 |
| 4,531,058 | 7/1985 | Burnham et al. . |
| 4,593,198 * | 6/1986 | Pang et al. ............................ 250/366 |
| 4,743,764 | 5/1988 | Casey et al. . |
| 4,749,863 | 6/1988 | Casey et al. . |
| 4,750,972 | 6/1988 | Casey et al. . |
| 5,430,406 * | 7/1995 | Kolodziejczyk ..................... 327/336 |
| 5,471,061 | 11/1995 | Moyers et al. . |
| 5,514,870 * | 5/1996 | Langenbrunner ..................... 250/367 |
| 5,750,991 * | 5/1998 | Moyers et al. .................. 250/363.03 |
| 6,087,663 * | 7/2000 | Moisan et al. ........................ 250/367 |
| 6,160,259 * | 12/2000 | Petrillo et al. ................... 250/363.07 |
| 6,215,122 * | 4/2001 | Clifford et al. ....................... 250/369 |

OTHER PUBLICATIONS

M.E. Phelps, et al.: "*Positron Emission Tomography and Audiography*", Raven Press, 1986; pp. 209–271.

J.C. Moyers: "*A High Performance Detector Electronics System for Positron Emission Tomography*", Masters Thesis, University of Tennessee, Knoxville, TN, 1990.

S.R. Cherry, et al.: "3–D PET Using a Conventional Multislice Tomograph Without Septa", JI. C.A.T., 15(4) 655–668.

C.L. Morris, et al.: "A Digital Technique for Neutron–Gamma Pulse Shape Discriminator", Nuclear Inst. and Methods, 137 (1976) 397–398.

M. Dahlbom, et al.—Performance of a YSO/LSO Phoswich Detector for use in a PET/SPECT System IEEE Transaction on Nuclear Science, vol. 44, No. 3, Jun. 1997, pp 1114–1119.

\* cited by examiner

*Primary Examiner*—Constantine Hannaher
*Assistant Examiner*—Albert Gagliardi
(74) *Attorney, Agent, or Firm*—Pitts & Brittian, P.C.

(57) ABSTRACT

A system and method of reducing pile-up errors in multi-crystal tomography applications. In a system with multi-crystal gamma ray detectors having scintillating crystals with different decay constants, the problem of signal pile-up is avoided by taking energy samples during a fast integration time and stopping the integration process if the sampling indicates that the event occurred in the crystal with the faster decay time, and continuing the integration process if the sampling indicates that the event occurred in the crystal with the slower decay time.

34 Claims, 11 Drawing Sheets

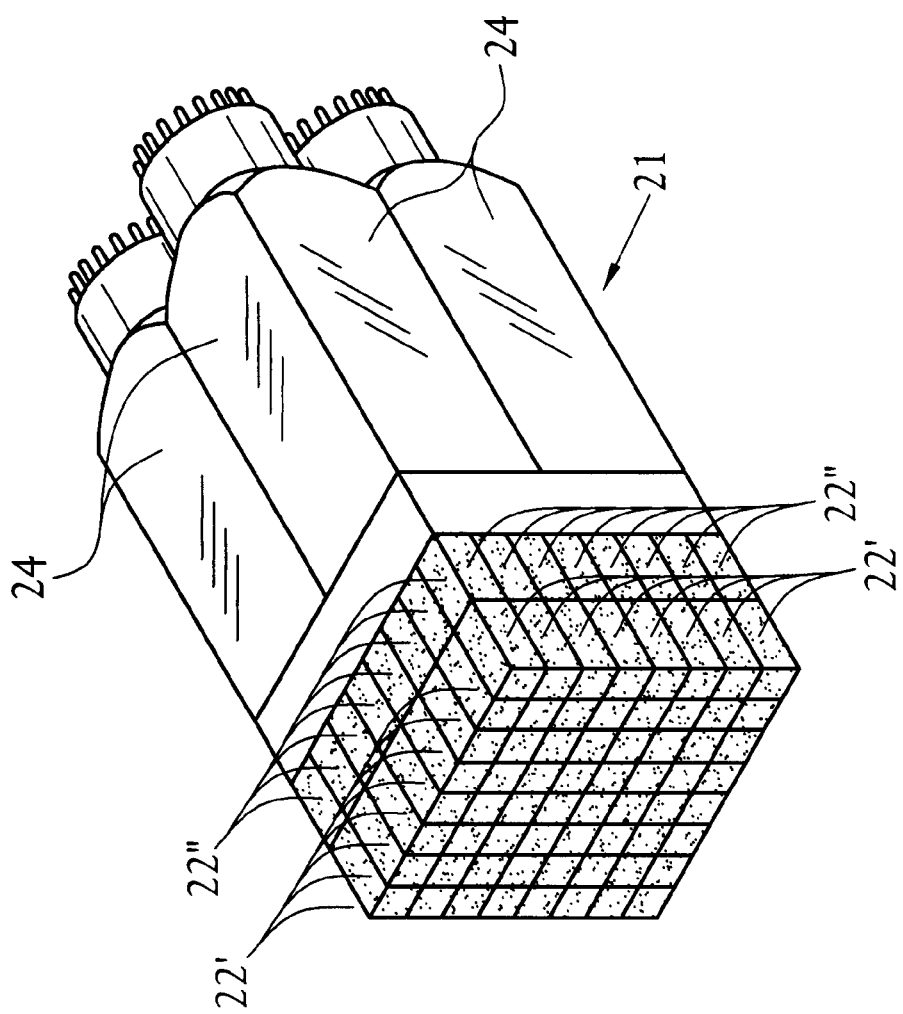

Block Diagram of Gated Integrator

Block Diagram of Digital Integration

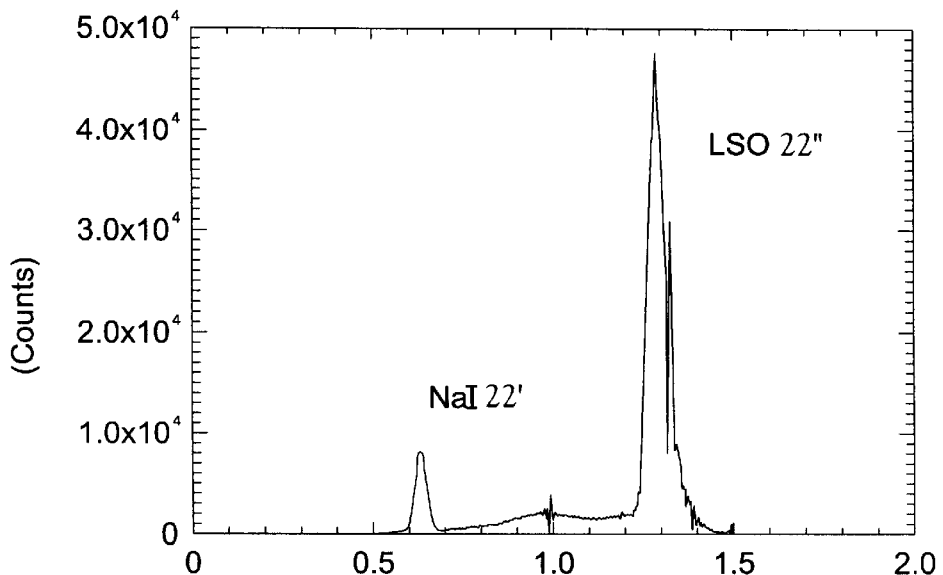

(Ratio Space of 1st Energy Sample /2nd Energy Sample) ($E_1/E_2$)
Condition of Low Count Rate in Fast Crystal
Using Integration Time Based Upon the Slow Decay Crystal

Fig.10(a)

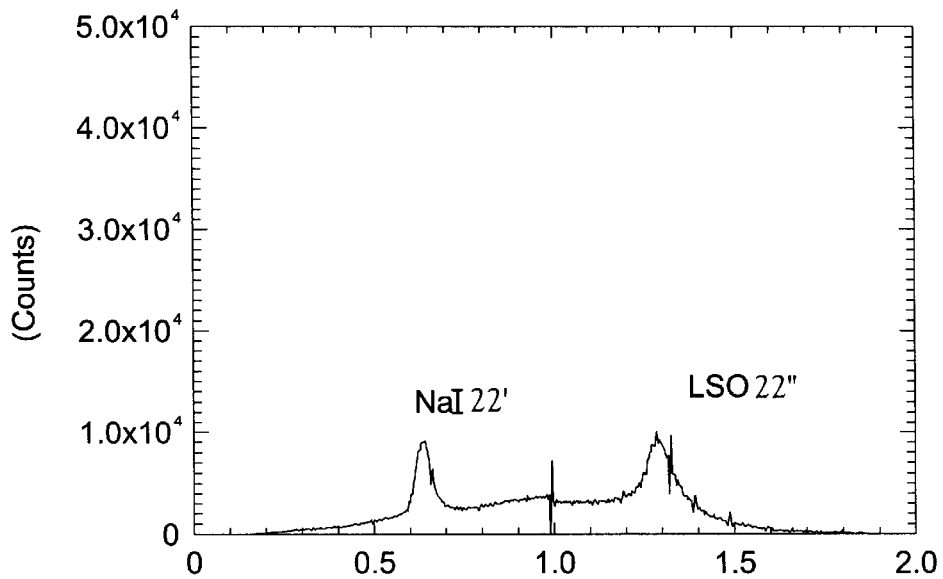

(Ratio Space of 1st Energy Sample /2nd Energy Sample) ($E_1/E_2$)
Condition of High Count Rate in Fast Crystal
Using Integration Time Based Upon the Slow Decay Crystal
Producing Misclassification of Crystal Type

Fig.10(b)

(Ratio Space of 1st Energy Sample /2nd Energy Sample) ($E_1/E_2$)
Comparison of Low, Medium and High Count Rate Conditions in Fast Crystal
Using Integration Time Based Upon the Slow Decay Crystal
Producing Greater Misclassification of Crystal Type as Count Rate Increases

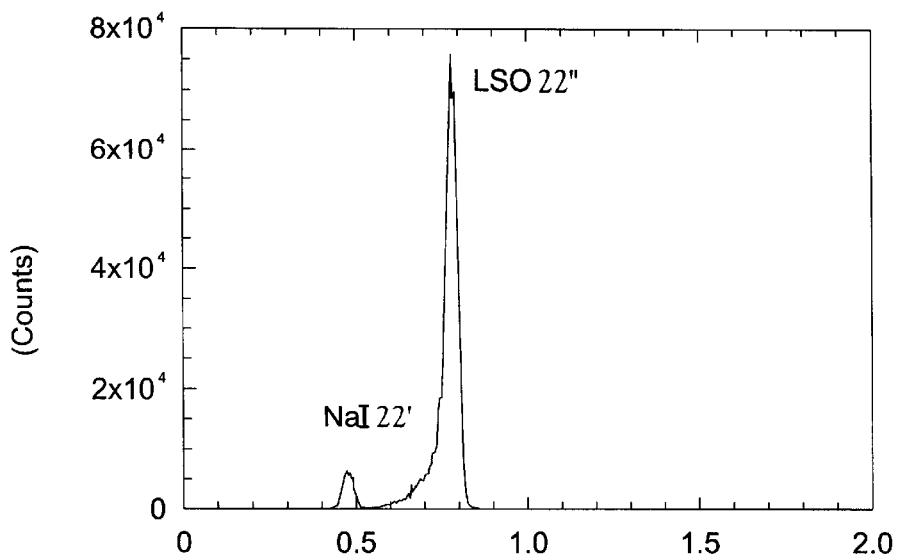

(Ratio Space of 1st Energy Sample / 2nd Energy Sample) ($E_1/E_2$)
Condition of Low Count Rate in Fast Crystal
Using Optimal Integration Time, Causing no Misclassification of Crystal Type

Fig.13(a)

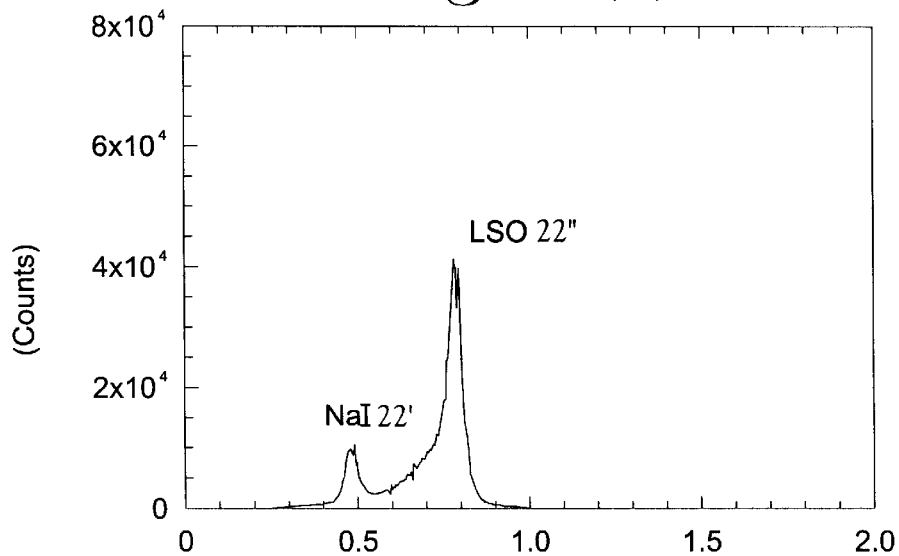

(Ratio Space of 1st Energy Sample / 2nd Energy Sample) ($E_1/E_2$)
Condition of High Count Rate in Fast Crystal
Using Optimal Integration Time, Causing no Misclassification of Crystal Type
Due to Pile-Up

Fig.13(b)

(Ratio Space of 1st Energy Sample / 2nd Energy Sample) ($E_1/E_2$)
Comparison of Low, Medium and High Count Rate in Fast Crystal
Using Optimal Integration Time, Causing no Misclassification of Crystal Type
Due to Pile-Up

SYSTEM AND METHOD FOR REDUCING PILE-UP ERRORS IN MULTI-CRYSTAL GAMMA RAY DETECTOR APPLICATIONS

TECHNICAL FIELD

This invention relates to the field of gamm ray detection. More specifically, the present invention relates to a system and method for reducing the pile-up of detected gamma ray events in a multi-decay time detector in emission tomograph devices. Although described specifically for pile-up rejection in positron emission tomography, the invention is applicable for various purposes in other tomograph devices. It is also more generally useful for multi-scintillation nuclear detection systems whereby pile-up related errors are reduced through the dynamic selection of integration times.

BACKGROUND ART

Positron Emission Tomography (PET) is a nuclear imaging technique used in the medical field to assist in the diagnosis of diseases. In PET, short-lived positron-emitting isotopes, referred to as radiopharmaceuticals, are injected into a patient. When these radioactive drugs are administered to a patient, they distribute within the body according to the physiologic pathways associated with their stable counterparts. For example, the radiopharmaceutical $^{18}$F-labeled glucose, known as fluorodeoxyglucose or "FDG", can be used to determine where normal glucose would be used in the brain. Other radioactive compounds suitable for PET scanning include $^{11}$C-labeled glucose, $^{13}$N-labeled ammonia and $^{15}$O-labeled water.

As the FDG or other radiopharmaceutical isotopes decay in the body, they discharge positively charged particles called positrons. Upon discharge, the positrons encounter electrons, and both are annihilated. As a result of each annihilation event, gamma rays are generated in the form of a pair of photons approximately 180 degrees (angular) apart. These occurrences can be mapped within the patient's body, thus allowing for the quantitative measurement of metabolic, biochemical and functional activity in living tissue. More specifically, PET images (often in conjunction with an assumed physiologic model) can be used to evaluate a variety of physiologic parameters such as glucose metabolic rate, cerebral blood flow, tissue viability, oxygen metabolism and in vivo brain neuron activity.

Positron Emission Tomography (PET) has gained significant popularity in nuclear medicine because of the ability to non-invasively study physiological processes within the body. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology and neurology.

As noted, PET data acquisition occurs by detection of both photons emitted from the annihilation of the positron in a coincidence scheme. Due to the approximate 180 degree angle of departure from the annihilation site, the location of the two detectors registering the "event" define a chord passing through the location of the annihilation.

By histogramming these lines of response (the chords), a "sinogram" is produced that may be used by a process of back-projection to produce a two dimensional image of the activity. Detection of these lines of activity is performed by a coincidence detection scheme. A valid event line is registered if both photons of an annihilation are detected within a coincidence window of time. Coincidence detection methods ensure (disregarding other second-order effects) that an event line is histogrammed only if both photons originate from the same positron annihilation.

Another tomography diagnostic system has been developed, known as single photon emission computed tomography (SPECT). The SPECT apparatus is similar to a PET system, except that instead of analyzing photon pairs, the SPECT system analyzes single photons emitted from the positron annihilations detected within the patient. It is now possible for a single tomography system to employ both PET and SPECT technologies.

Traditionally, positron emission tomography systems have employed discrete scintillators arranged in rings. The scintillators are comprised of materials suitable for interacting with gamma rays, including bismuth germanium crystals (BGO), lutetium oxyorthosilicate crystals (LSO), and sodium iodide crystals (NaI). Typically there are hundreds of detectors per ring, with one to 100 rings in the detector structure. Data is collected through two-dimensional acquisition of photon emission events. Recent advances in the art have permitted three-dimensional, or 3-D acquisition of data using an assortment of discrete scintillators.

The details of carrying out a PET study are given in numerous publications. Typically, the following references provide a background for PET. These are incorporated herein by reference for any of their teachings.

1. M. E. Phelps, et al.: "Positron Emission Tomography and Audiography", Raven Press, 1986;
2. R. D. Evans: "The Atomic Nucleus", Kreiger, 1955;
3. J. C. Moyers: "A High Performance Detector Electronics System for Positron Emission Tomography", Masters Thesis, University of Tennessee, Knoxville, Tenn, 1990;
4. U.S. Pat. No. 4,743,764 issued to M. E. Casey, et al, on May 10, 1988;
5. S. R. Cherry, et al.: "3-D PET Using a Conventional Multislice Tomograph Without Septa", JI. C.A.T., 15(4) 655–668; and
6. C. L. Morris, et al.: "A Digital Technique for Neutron-Gamma Pulse Shape Discriminator", Nuclear Inst. and Methods, 137 (1976) 397–98.

It is desirable for the customer and, derivatively, the patient for the cost of PET scanner systems to be reduced. Cost reductions have been achieved through the use of block detectors. The block detectors allow for a reduction in the number of photomultiplier tubes (PMT) required to properly detect the gamma ray interaction location. In this arrangement, more crystals are enabled to share each PMT.

Another advance in PET is the ability to determine the depth of interaction of the gamma ray in the detector. The depth information is used to correct the line of response determination due to the penetration depth of oblique angle gamma rays on large area detectors. This parallax problem arises at the edge of the field of view on large area detectors and in ring tomographs. To determine the depth of interaction of a gamma ray in a detector, a special detector composed of two or more different decay time scintillating crystals is used. In this arrangement, the crystals are placed on top of each other from front to back. The depth of interaction of each gamma ray is determined by analyzing the light decay properties of the detected scintillations to determine the crystal in which the gamma ray interacted; i.e., at the front or the back of the crystal arrangement. The gamma ray interaction depth is used in the image reconstruction to correct the line of response parallax.

At present, there are multi-crystal tomography imaging systems which employ two scintillating crystals in the detector. These dual crystal detector arrangements are referred to as phoswitch detectors. Reasonable costs, high light output, and fast decay time scintillating crystals have made phoswitch detectors commercially and technologically practical. However, a data collection problem arises in connection with the use of dual crystal detectors. That problem is based on the different decay times incident in the two crystals. Those skilled in the art will understand that crystals having different decay times will necessarily have different optimal integration times for carrying out the signal processing process. More specifically, the optimal integration time is longer for the slow crystal than for the fast crystal. However, a longer integration time creates a circumstance wherein multiple gamma rays may be incident on the fast crystal during the integration process, causing a "pile-up" of gamma ray events. This, in turn, can cause the sampling of multiple events within the fast crystal to be misinterpreted as a single gamma ray event within the slow crystal. The result is that the image reconstruction used to correct the line of response parallax will report an incorrect position.

The problem of pile-up is compounded when phoswitch detectors are used in a block configuration. Those skilled in the art understand that annihilation events in connection with PET occur randomly. Due to the large area of the detector, multiple gamma rays may be incident on the individual detectors during the integration time, that is, the period in which gamma rays are analyzed. The use of large area detectors increases the probability that one gamma ray will interact with a scintillating crystal while the signal resulting from an earlier gamma ray is still being processed, i.e., during the "dead time."

Accordingly, it is an object of the present invention to provide a system and method for reducing pile-up errors in dual crystal tomography applications.

It is a further object of the present invention to provide a system and method for reducing pile-up errors in multi-crystal structures for PET scanning systems having block crystal configurations.

Another object of the present invention is to provide a system and method for reducing pile-up of signal data in connection with single photon emission computed tomography (SPECT) systems.

DISCLOSURE OF THE INVENTION

Other objects and advantages of the present invention will become more apparent upon reviewing the detailed description and associated figures of the method for reducing pile-up errors in dual crystal tomography. In the PET Scanning System of the present invention, a series of scintillation detectors are utilized, with each detector having two different decay time crystals in the detector head. One crystal within the detector head employs a slower decay time, while the second crystal employs a faster decay time.

The light generated from the respective scintillator crystals is converted to a signal which is proportional to the amount of light generated by the incident gamma rays. That signal is then integrated using a gated integrator or digital summation of the sample energy waveform. The rate of light collection is then be determined by taking samples of the integrated signal.

A shape discriminator is provided in order to determine whether a gamma ray was detected in the fast or in the slow crystal. The optimal integration time for each crystal is different, with the optimal integration time being longer for the slow crystal in order to afford more time to acquire light. However, the use of a longer integration time increases the probability of a pile-up of gamma ray events within the detector. This, in turn, can cause sampling of multiple events within the fast crystal to be misinterpreted as a single gamma ray event within the slow crystal.

In order to avoid misclassification of the gamma ray events caused by pile-up, the present invention presents a method in which the crystal type is identified by taking the energy samples during the fast crystal integration time, and then stopping the integration if the fast crystal is identified. If the slow crystal is identified, then the integration time is continued in order to acquire a higher percentage of light from the slow crystal. Fast crystal events are not misclassified as slow crystal events since the crystal type is identified based on the fast crystal integration time. The result is that the percentage of pile-up events from the fast crystal is reduced simply by reducing the integration time.

BRIEF DESCRIPTION OF THE DRAWINGS

FIG. 3 is a perspective view of a phoswitch detector utilized in positron emission tomography, with dual crystals shown.

FIGS. 10(a), 10(b) and 10(c) present shape histograms showing counts as a function of the ratio of the first energy sample to the second energy sample ($E_1/E_2$). In the plot of FIG. 10(a), there is a small amount of pile-up in the fast crystal, but with the classification of events nevertheless accurate. However, in the plot of FIG. 10(b), there is a condition of high count rate, causing a clear misclassification of events due to pile-up. FIG. 10(c) presents a shape histogram showing conditions of low, high, and medium count rate in the fast decay time crystal.

FIGS. 13(a), 13(b) and 13(c) present shape histograms showing counts as a function of the ratio of the first energy sample to the second energy sample ($E_1/E_2$). In each figure, the classification of events is proper. In the plot of FIG. 13(a), there is a low count rate condition in the fast crystal; in the plot of FIG. 13(b), there is a condition of high count rate; and in FIG. 13(c), the shape histograms show conditions of low, high, and medium count rate in the fast decay time crystal. The gamma ray events are not misclassified due to pile-up.

BEST MODE FOR CARRYING OUT THE INVENTION

Figure 1:
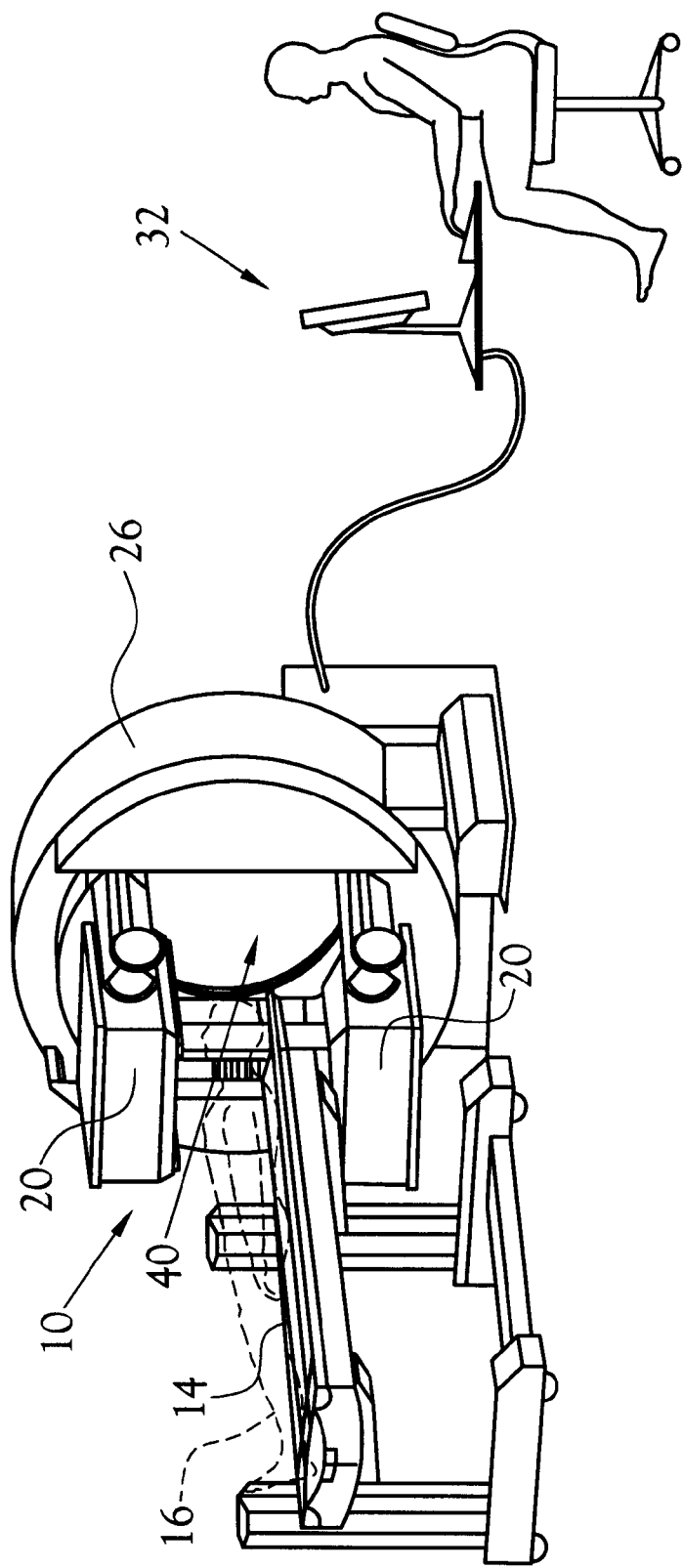
FIG. 1 is a perspective view of a positron emission tomography scanner.

A perspective view of a positron emission tomography system 10 is shown generally in FIG. 1. The PET system 10 includes a housing 26 for carrying a configuration of detectors 20. In this embodiment of the PET Scanning system 10, the housing 26 is a gantry 26 which is rotatably mounted about a horizontal axis. A computer generally indicated at 32 is electrically connected to the scanning system 10 and serves to control the movement and electronic controls normally associated with a scanning system 10 such as the drives for rotating the gantry 26 about a horizontal axis.

In order to produce a body-section tomographic image of a selected portion of a patient's 16 body, the patient 16 is moved into the patient opening 40 by means of a gurney 14. A radiopharmaceutical is normally administered to the patient 16 prior to movement into the patient opening 40. When these radioactive drugs are administered to a patient 16, they distribute within the body according to the physiologic pathways associated with their stable counterparts. As the radioactive isotopes decay in the body, they discharge positrons. These positrons each combine with an electron and are annihilated. As a result of each annihilation event, gamma rays are generated in the form of a pair of photons which are given off in opposite directions, or a direction separated by approximately 180 degrees. (see FIG. 2) Detection of the presence, direction of travel, and distribution of the photons, provides information necessary to generate a tomographic image of a body-section or section of another living organism positioned within the scanning system 10.

FIG. 3 is a perspective view of a phoswitch detector 21 utilized in positron emission tomography. The phoswitch detector 21 utilizes two crystals 22' and 22", one being a front crystal 22' and the other being a back crystal 22". In the preferred embodiment, each of the two crystals 22", 22" employs a different decay time. Typically, the front crystal 22' defines a scintillation member having a slower decay time such as NaI, while the back crystal 22" defines a scintillation material having a faster decay time, such as LSO. Each of the individual scintillating crystals 22" having a faster decay constant is associated with a corresponding scintillating crystal 22' having a slower decay constant. Those skilled in the art will understand that the order of the scintillation members is interchangeable. In addition, the detector may employ more than two scintillating crystals, with each having a different decay constant, to further enhance resolution of the tomographic image.

Figure 2:
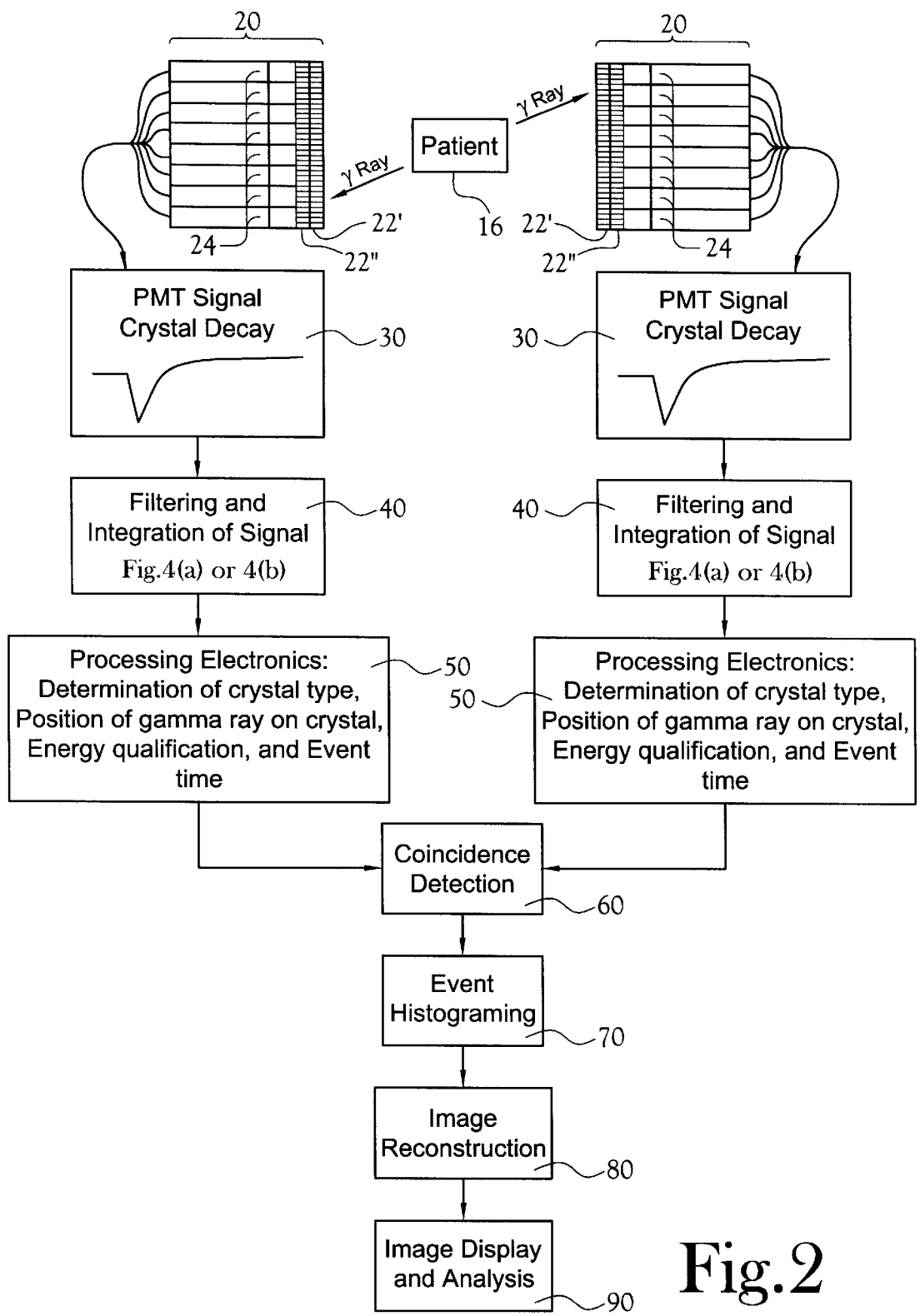
FIG. 2 is a block diagram showing the steps for signal processing in connection with positron emission tomography.

As shown in FIG. 3, the scintillating crystals 22' and 22" are arranged in an array having a selected number of rows and columns within the detector configuration 20 of FIG. 1. Multiple phoswitch detectors are employed to create a block detector configuration 20. FIG. 2 depicts side views of detector configurations 20 having a block arrangement. In the preferred embodiment, the fast and slow crystals 22' and 22" are aligned one in front of the other throughout the array 20. However, those skilled in the art will understand that other alignments are viable, including the use of a single element for both fast and slow crystals 22' and 22" in which the detector has a continuous light guide.

The phoswitch detector in FIG. 3 also shows the position of photomultiplier tubes 24 in the detector block 21. The photomultplier tubes 24 serve as photon converters to convert light into pulses of electrical energy. Those skilled in art will understand that avalanche photo diodes or other photon converting transducers could be used in lieu of photomultiplier tubes 24. In the embodiment presented in FIG. 3, each photomultiplier tube 24 can service a number of scintillating crystals 22' and 22".

In accordance with PET technology, the detectors 20 are positioned around the patient 16 as shown in FIG. 1. The detectors 20 receive gamma rays emitted from the positron annihilation events. These gamma rays, in turn, interact with the two scintillator crystals 22' and 22", creating a flash of light. Each flash of light is then converted to an electrical pulse by the photomultiplier tube 24. The electrical pulse is proportional to the amount of light given off by the scintillator crystals 22' and 22". Data comprising the number and position of gamma ray rate interactions within the various detectors 20 are then compiled, allowing a mapping of events within the patient's body to be created. This mapping is referred to as a tomographic image.

A more accurate tomographic image is created when the depth of interaction of each gamma ray within the detector 20 is determined. The depth of interaction of the gamma ray is determined by analyzing the light decay properties of the detected event to determine if the gamma ray interacted at the front 22' or the back 22" crystal. he depth information is used to correct the line of response determination due to the penetration depth of oblique angle gamma rays on large area detectors. This parallax problem arises at the edge of the field of view on large area detectors and in ring tomographs. The problem of parallax is overcome through the use of the dual crystal detectors 20.

In order to determine the difference in the light decay between the front 22' and back 22" crystals, the light from the scintillator 22' or 22" is first converted to an electrical pulse, or signal 30, by the photomultiplier tube 24. As noted, the electrical signal 30 is proportional to the amount of light given off by the scintillator crystals 22' and 22". The electrical signal 30 is then processed through a series of signal processing steps. State of the art signal processing is by means of a digital signal processor which is programmed through source code. A flow chart presenting the sequence of signal processing steps for tomographic applications is shown in FIG. 2.

Figure 4A:
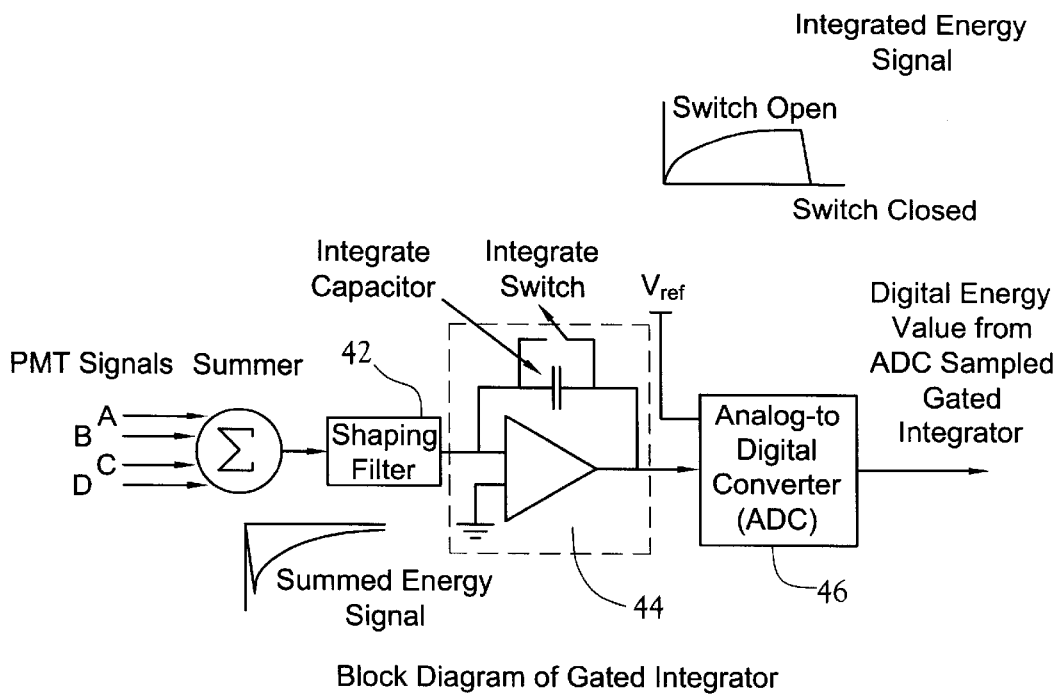
FIG. 4(a) is a block diagram showing steps for signal filtering and integration using a gated integrator.
Figure 4B:
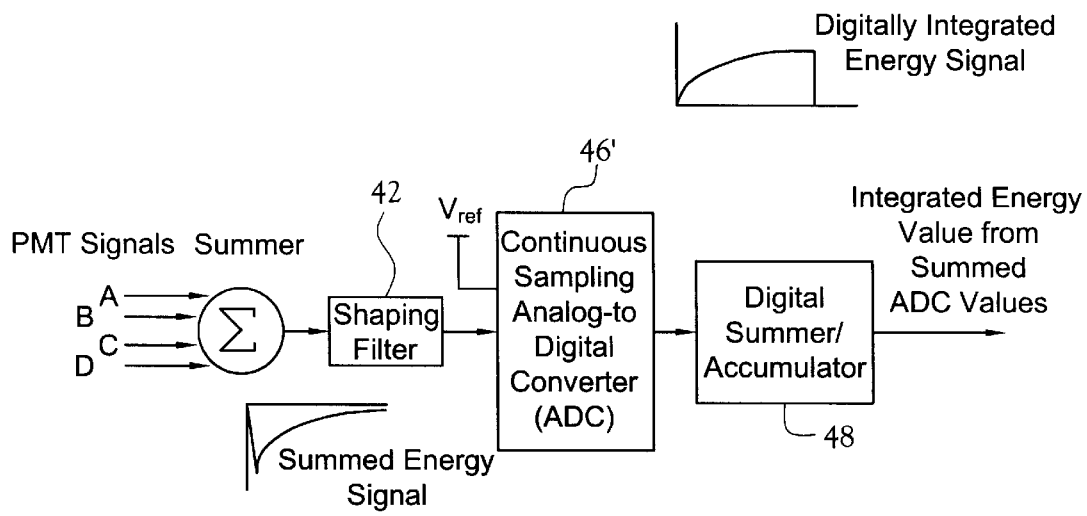
FIG. 4(b) is a block diagram showing steps for signal filtering and integration using digital summation.

The first step in processing the electrical signal 30 is the integration of the signal 30. Integration can be accomplished through either analog or digital means. FIG. 4(a) presents a block diagram of a gated integrator which employs integrator circuit 44 as an analog integrator. FIG. 4(b) presents a block diagram for performing a digital summation of the sampled filtered PMT waveform using a continuous sampling analog-to-digital converter 46' and a digital summer/ accumulator 48. The result in either embodiment is a digital value representing an amount of energy from a detected gamma ray event.

Figure 5:
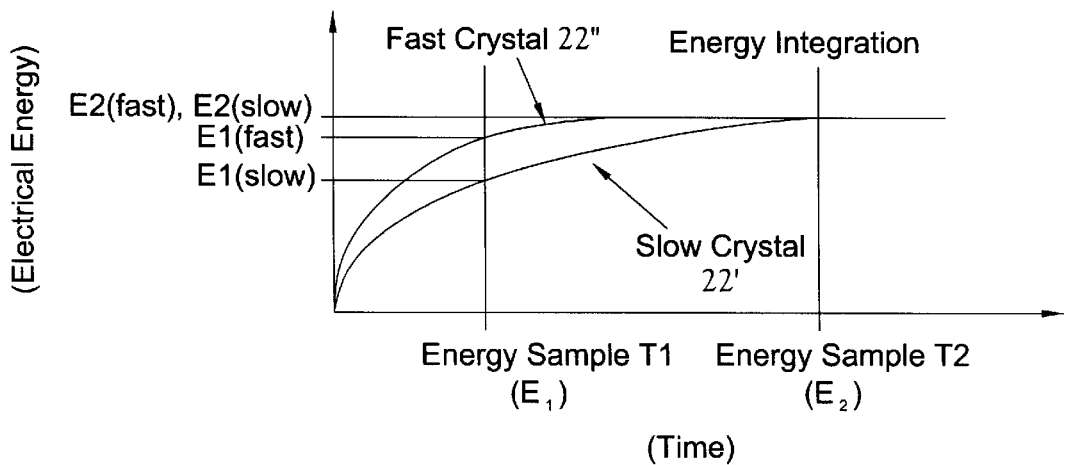
FIG. 5 is a Cartesian coordinate depicting integrated signals for scintillating crystals having two different decay times. In this plot, energy is a function of time.

As part of the integration process, an appropriate integration time must be selected. The integration time is determined by the light decay time of the scintillating crystal 22' or 22" and the percentage of the total crystal light output that is used for the energy and position determination. The integrated signal output for the two different decay time crystals are shown in FIG. 5.

Some time after initiating integration, the integrated energy signals are sampled. In the embodiment illustrated in FIG. 4(b), a flash analog-to-digital converter (ADC) 46' is used. In this manner, the quantity of light collected within a detector can be determined. As shown in FIG. 5, energy samples are taken at time T1 and again at time T2 to determine the rate of light decay within the scintillating crystal. The ratios of the energies $E_1$ and $E_2$ ($E_1/E_2$) are then used to determine if the gamma ray event occurred in the fast 22" or the slow 22" crystal. A review of FIG. 6 will show that the ratio of $E_{1\ to\ E2}$ will be smaller for the slower crystal 22' than for the faster crystal 22".

Figure 6:
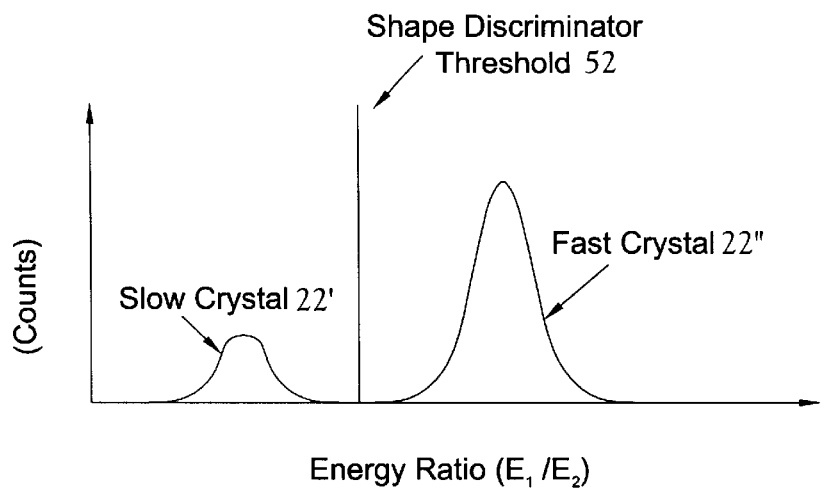
FIG. 6 is a Cartesian coordinate depicting the histogram of the ratio of a first energy sample divided by a second energy sample for slow and fast crystals. Counts are depicted as a function of energy ratios ($E_1/E_2$).

In a dual crystal tomography system, a shape discriminator 52 determines whether the gamma ray interaction portrayed by the sampled signal occurred within the slow crystal 22' or the fast crystal 22". A generalized histogram of this process is depicted in FIG. 6. In the system of the prior art, this determination is made after the integration process. However, the determination can prove to be inaccurate in the event of signal pile-up within the fast crystal 22".

One option for reducing the probability of signal pile-up is to decrease the time in which the integration process takes place. Those skilled in the art will understand that the longer the integration time, the greater the probability of a pile-up event from another gamma ray occurring. On the other hand, the use of a shorter integration time compromises the quality of the gamma ray energy measurement and interaction position determination. This problem is compounded when phoswitch detectors 21 are employed, since phoswitch detectors 21 are composed of crystals with different light decay constants having different optimal integration times.

Figure 7:
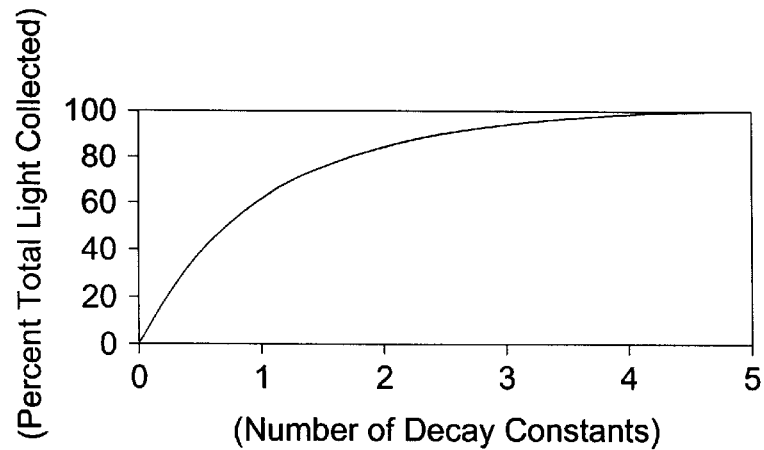
FIG. 7 is a Cartesian coordinate presenting the percent of total light collected as a function of the integration time (in terms of decay constants) is shown for a decay signal.

The advantages of an optimally short integration time for the fast scintillating crystal 22" are lost if the integration time must be sufficient to support acquiring most of the light from the slow decay constant scintillating crystal 22'. The technique to regaining the optimally short integration time for the fast crystal 22" is to quickly identify the short decay time crystal and adjust the integration time based on the crystal type. The amount of light collected versus the integration time (in decay constants) is shown in FIG. 7. Typically, eighty to ninety percent of the light is integrated to optimize energy resolution and crystal positioning versus processing (dead) time. Therefore, the light is typically integrated for approximately two and a half to five decay constants.

Figure 8:
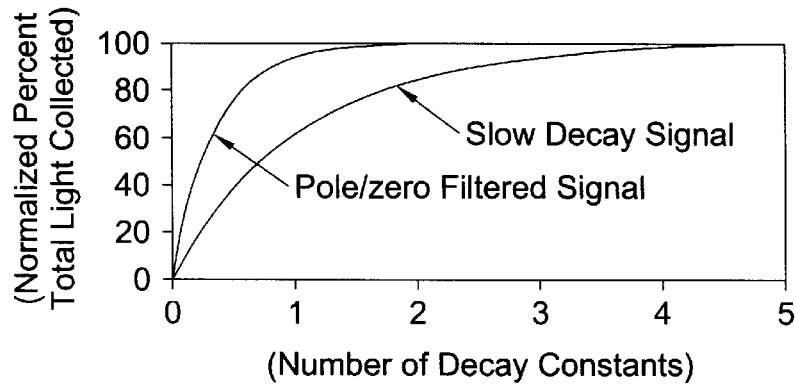
FIG. 8 is a Cartesian coordinate presenting the normalized percent of total light collected versus the number of scintillator decay constants for both a filtered and an unfiltered slow decay signal. This figure shows the effect of adding a pole/zero filter with the "zero" time constant matched to the slow crystal to change the effective decay time constant.
Figure 9:
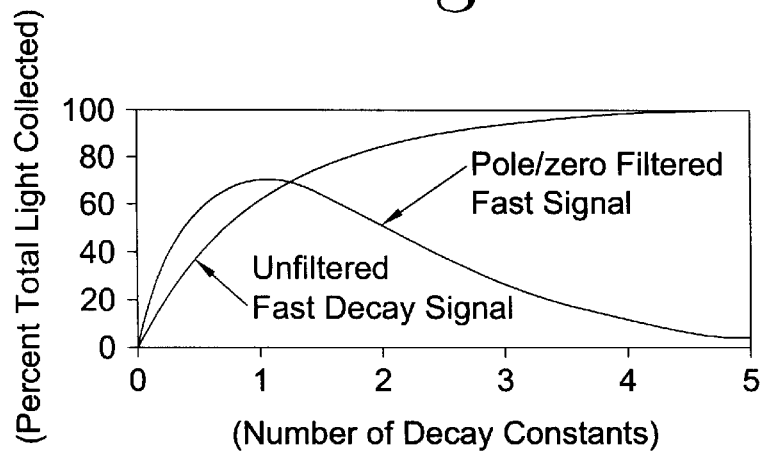
FIG. 9 is a Cartesian coordinate presenting the percent of total light collected versus the number of scintillator decay constants for both a filtered and an unfiltered fast decay signal. This figure shows the effect of adding a pole/zero filter on the fast signal with the "zero" time constant matched to the slow crystal.

The integration time of a scintillating crystal 22' or 22" can be shortened causing the energy resolution and crystal positioning to degrade. The likelihood of the processing electronics 50 re-triggering due to the remaining light being emitted by the crystal 22' or 22" also increases as the integration time is shortened. To reduce the likelihood of retriggering during tomography, the effective decay time of the slow crystal 22' can be shortened by processing the signal with a pole/zero filter 42. Those skilled in the art will understand that by matching the filter's zero time constant with the decay time constant of the long decay crystal 22', the long decay time tail of the crystal 22' can be canceled out as shown in FIG. 8. The filter's pole time constant determines the resulting signal decay. However, using the pole/zero filter 42 on a phoswitch detector 21, with the zero matching the long decay time constant crystal 22', causes the signal of the short decay constant crystal 22' to distort as shown in FIG. 9. When this occurs, the position and energy information of the gamma ray event is deteriorated. To obtain the best position and energy information of the gamma ray event, the energy sample of the signal is selected to be at the peak of the signal response.

To avoid the problem of pile-up, the typical system simply discards pile-up events. However, this causes the efficiency of the PET Scanner 10 to be degraded. On the other hand, if a pile-up event is not detected or discarded, the light output from the second gamma ray event is added to the integrated energy from the first event. The result of the pile-up events is improper calculation of the energy and position of both events. When a pole/zero filter 42 is used to reduce retriggering of the electronics 50, a pile-up event can cause misclassification of the crystal type (fast or slow decay time).

Figure 10C:
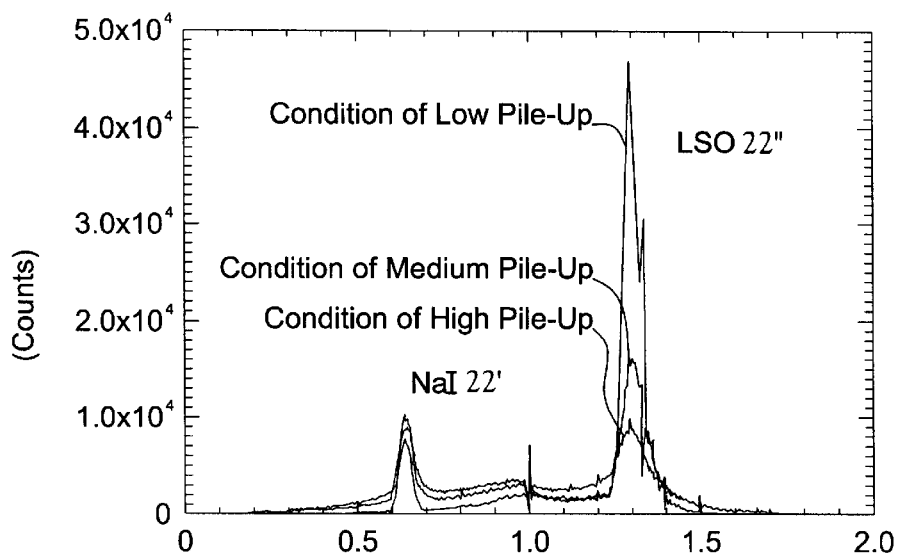
Figure 11:
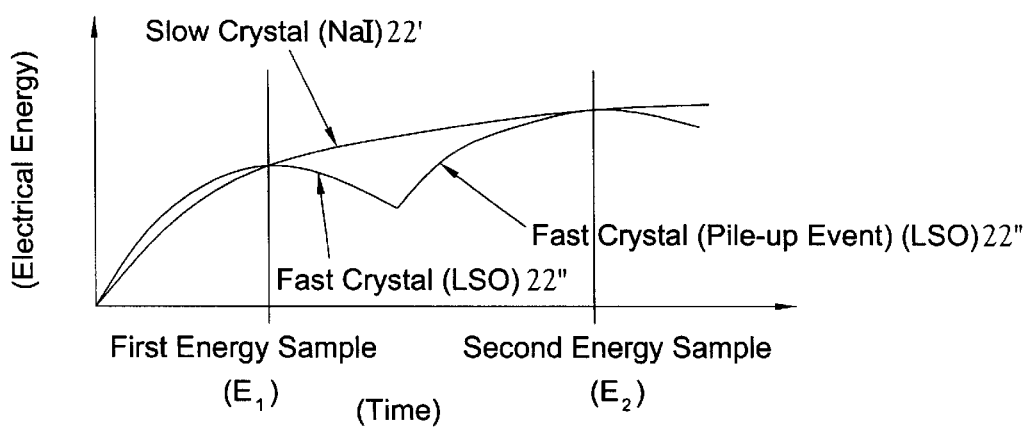
FIG. 11 depicts a pile-up event in the fast scintillator causing misclassification of the crystal decay time due to sampling the energy at the slow crystal integration time rather than at the fast crystal integration time.

FIGS. 10(a), 10(b) and 10(c) present shape histograms showing counts as a function of the ratio of the first energy sample to the second energy sample ($E_1/E_2$). FIG. 10(c) presents a shape histogram showing conditions of low, high, and medium count rate in the fast decay time crystal (LSO). The plot of FIG. 10(a) isolates the condition of low count rate in the fast crystal 22" and a small amount of pile-up, but with the classification of events nevertheless accurate. As the activity in the detector 20 increases, the number of pile-up events increase causing more events to be misclassified as the slow crystal 22'. In the plot of FIG. 10(b), the condition of high count rate is isolated, showing a clear misclassification (NaI instead of LSO) of gamma ray events due to pile-up. Since the ratio of detected gamma rays in each of the scintillators 22' and 22" is determined by the density of the materials, the change in the ratio of fast crystal 22" (such as LSO) to slow crystal 22' (such as NaI) detected events is due to misclassification of LSO pile-up events. The result is multiple fast crystal 22" events being misinterpreted as a single slow crystal 22' event, shown in FIG. 11.

According to the present invention, the misclassification of fast crystal events caused by pile-up is reduced by taking two energy samples during the fast crystal 22" integration time, and then stopping the integration process if the fast crystal 22" is identified. If the slow crystal 22' is identified, then the integration continues in order to acquire a higher percentage of light from the slow crystal 22'. The percentage of pile-up events from the fast crystal 22" is thus reduced by the reduced integration time.

Figure 12A:
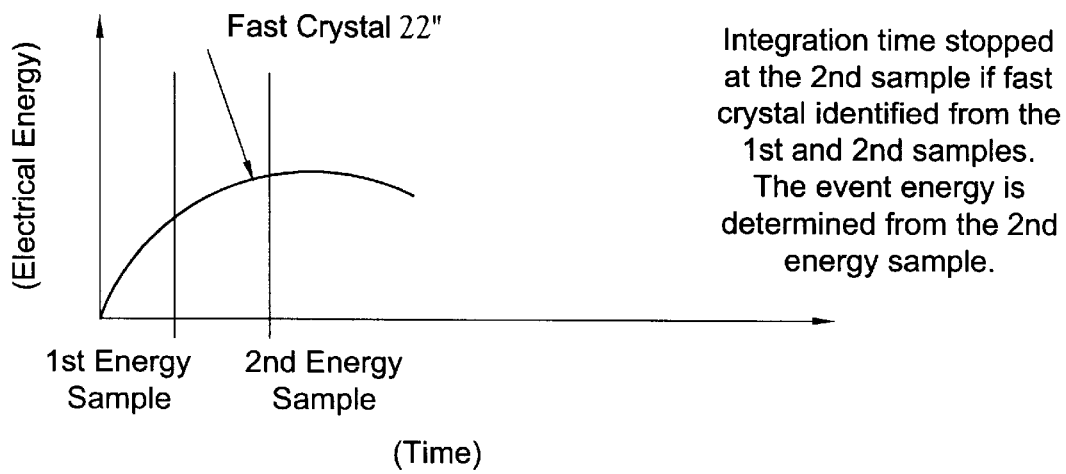
FIG. 12(a) and FIG. 12(b) graphically demonstrate the method of the present invention whereby the first and second energy samples are taken during the integration time for the scintillating crystal having the faster decay constant, with the integration being stopped if the faster crystal is detected in order to reduce pile-up, but continued if the slower crystal is detected.
Figure 12B:
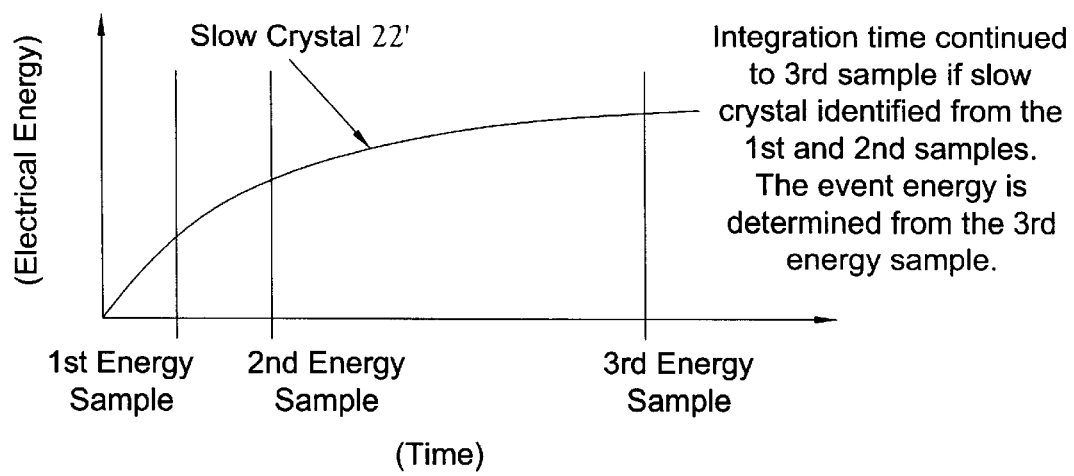

Under the method of the present invention, fast crystal 22" events are not misclassified as slow crystal 22' events due to pile-up at high count rates since the crystal type is identified based on the fast crystal 22" integration time. FIG. 12(a) shows the fast crystal 22" identified, with the integration then stopping. FIG. 12(b), on the other hand, shows the slow crystal 22' being identified, with the integration then continuing for the slow crystal 22" integration time.

Figure 13C:
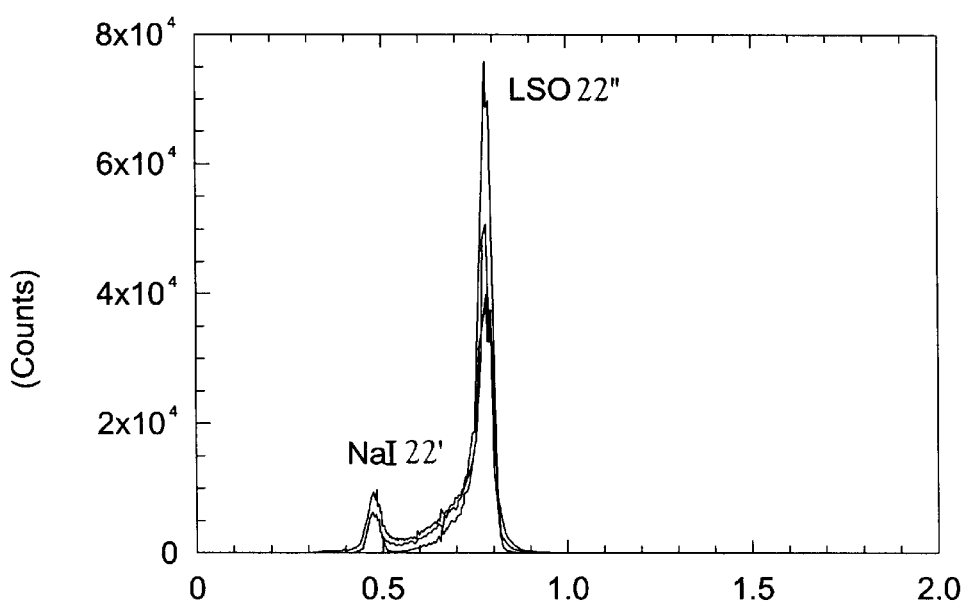

FIGS. 13(a), 13(b) and 13(c) present shape histograms showing counts as a function of the ratio of the first energy sample to the second energy sample ($E_1/E_2$). In the plot of FIG. 13(a), there is a low count rate condition in the fast crystal 22"; in the plot of FIG. 13(b), there is a condition of high count rate in the fast crystal 22"; and in FIG. 13(c), the shape histograms compare conditions of low, high, and medium count rate in the fast decay time crystal 22". In each figure, the classification of events is proper. The gamma ray events are not misclassified due to high count rate pile-up, the result being a proper correction of the parallax problem. Tomography then continues with more accurate coincidence detection 60, event histogramming 70, image reconstruction 80, and image display and analysis 90.

Those skilled in the art will understand that pile-up events which occur during the integration time of the slow crystal are discarded by the upper energy threshold as is common practice in PET scanners.

While a preferred embodiment for dual crystal tomography has been shown and described, it will be understood that it is not intended to limit the disclosure, but rather it is intended to cover modifications and alternate methods falling within the spirit and the scope of the invention as defined in the appended claims. As noted previously, the system and method presented herein is applicable not only to dual crystal tomography detectors, but also to tomography detectors which employ a plurality of scintillating crystals. In the instance of multicrystal detectors, two energy samples are taken during the optimal integration time for the fastest of the associated crystals, with integration being stopped if the fastest crystal is identified. If the fastest decay time crystal is not identified, the integration process continues, but with an additional energy sample being taken at the optimal integration time for the identified crystal. If the slowest crystal is identified, then the integration continues in order to acquire a higher percentage of light from the slowest crystal. Errors due to pile-up events from the fastest crystal or any intermediate crystal is thus reduced by the reduced integration time for gamma ray events occurring in those crystals.

The system and method of the present invention is equally useful in both positron emission tomography (PET) systems and to single photon emission computed tomography (SPECT) systems. In addition, the method of the present invention will find utility in non-tomographic applications where the detection and mapping of gamma rays is employed.

Having thus described the aforementioned invention, We claim:

1. A method for reducing pile-up errors in connection with the use of detectors having a plurality of scintillating crystals, the detectors receiving gamma rays, and each of the plurality of scintillating crystals having a different decay constant, said method comprising the steps of:

determining an appropriate integration time for each of said plurality of scintillating crystals, including an integration time for a first of said plurality of scintillating crystals having a first decay constant, and an integration time for each other of said plurality of scintillating crystals, determination of said appropriate integration time being based upon a light decay time of each of said plurality of scintillating crystals and a percentage of the total crystal light output required, and wherein said decay constant for each of said other of said plurality of scintillating crystals is slower than said first decay constant;

converting light generated by one of said plurality of scintillating crystals upon interaction with a gamma ray, into a pulse of electrical energy using a photon converter;

beginning integration of said pulse of electrical energy;

taking first and second samples of said pulse of electrical energy to determine a rate of light decay within one of said plurality of scintillating crystals, said first and second samples taken during the integration time selected for said first of said plurality of scintillating crystals having said first decay constant;

calculating the ratio of said first sampled pulse of electrical energy to said second sampled pulse of electrical energy to determine whether said gamma ray event occurred in said first of said plurality of scintillating crystals or in one of said other of said plurality of scintillating crystals having a slower decay constant, said ratio being larger for said first scintillating crystal than for any of said other scintillating crystals;

identifying in which of said plurality of scintillating crystals said gamma ray event occurred;

stopping said integration at said selected integration time for said first scintillating crystal having the faster decay constant if said gamma ray event is determined to have occurred in said first of said plurality of scintillating crystals; and continuing said integration for said selected integration time for said identified other of said scintillating crystals if said gamma ray event is determined not to have occurred in said first of said plurality of scintillating crystals, thereby acquiring a higher percentage of light.

2. The method of claim 1 wherein said photon converter used to accomplish said step of converting light generated by one of said plurality of scintillating crystals into a pulse of electrical energy is a photomultiplier tube.

3. The method of claim 1 wherein said photon converter used to accomplish said step of converting light generated by one of said plurality of scintillating crystals into a pulse of electrical energy is an avalanche photo diode.

4. The method of claim 1 wherein said integration of said pulse of electrical energy includes the use of a gated integrator.

5. The method of claim 1 wherein said integration of said pulse of electrical energy includes the use of a continuous sampling analog-to-digital converter and a digital summer/accumulator.

6. The method of claim 1 wherein said step of taking first and second samples of said pulse of electrical energy is accomplished by using an analog-to-digital converter.

7. The method of claim 1 wherein each of said plurality of scintillating crystals is fabricated primarily from lutetium oxyorthosilicate, and wherein each of said plurality of scintillating crystals has a different decay constant.

8. A method for reducing pile-up errors in a tomography system having a plurality of scintillating crystals in the detectors, the detectors receiving gamma rays, and each of the plurality of scintillating crystals having a different decay constant, said method comprising the steps of:

determining an appropriate integration time for each of said plurality of scintillating crystals, including an integration time for a first of said plurality of scintillating crystals having a first decay constant, and an integration time for each other of said plurality of scintillating crystals, determination of said appropriate integration time being based upon a light decay time of each of said plurality of scintillating crystals and a percentage of the total crystal light output required, and wherein said decay constant for each of said other of said plurality of scintillating crystals is slower than said first decay constant;

converting light generated by one of said plurality of scintillating crystals upon interaction with a gamma ray, into a pulse of electrical energy using a photon converter;

beginning integration of said pulse of electrical energy;

taking first and second samples of said pulse of electrical energy to determine a rate of light decay within one of said plurality of scintillating crystals, said first and second samples taken during the integration time selected for said first of said plurality of scintillating crystals having said first decay constant;

calculating the ratio of said first sampled pulse of electrical energy to said second sampled pulse of electrical energy to determine whether said gamma ray event occurred in said first of said plurality of scintillating crystals or in one of said other of said plurality of scintillating crystals, said ratio being larger for said first scintillating crystal than for any of said other scintillating crystals;

identifying in which of said plurality of scintillating crystals said gamma ray event occurred;

stopping said integration process at said selected integration time for said first scintillating crystal having the faster decay constant if said gamma ray event is determined to have occurred in said first of said plurality of scintillating crystals; and continuing said integration for said selected integration time for said identified other of said scintillating crystals if said gamma ray event is determined not to have occurred in said first of said plurality of scintillating crystals, thereby acquiring a higher percentage of light.

9. The method of claim 8 wherein said photon converter used to accomplish said step of converting light generated by one of said plurality of scintillating crystals into a pulse of electrical energy is a photomultiplier tube.

10. The method of claim 8 wherein said photon converter used to accomplish said step of converting light generated by one of said plurality of scintillating crystals into a pulse of electrical energy is an avalanche photo diode.

11. The method of claim 8 wherein said integration of said pulse of electrical energy includes the use of a gated integrator.

12. The method of claim 8 wherein said integration of said pulse of electrical energy includes the use of a continuous sampling analogto-digital converter and a digital summer/accumulator.

13. The method of claim 8 wherein said step of taking first and second samples of said pulse of electrical energy is accomplished by using an analog-to-digital converter.

14. The method of claim 8 wherein each of said plurality of scintillating crystals is fabricated primarily from lutetium oxyorthosilicate, and wherein each of said plurality of scintillating crystals has a different decay constant.

15. A method for reducing pile-up errors in a dual crystal tomography system, the tomography system having detectors with first and second scintillating crystals for receiving gamma rays, and the first scintillating crystal having a decay constant which is faster than the decay constant for the second scintillating crystal, said method comprising the steps of:

determining an appropriate integration time for said first scintillating crystal, determination of said appropriate integration time being based upon a light decay time of said first scintillating crystal and a percentage of the total crystal light output required for tomography;

determining an appropriate integration time for said second scintillating crystal, determination of said appropriate integration time being based upon a light decay time of said second scintillating crystal and a percentage of the total crystal light output required for tomography;

converting light generated by one of said first or second scintillating crystals upon interaction with a gamma ray, into a pulse of electrical energy using a photon converter;

beginning integration of said pulse of electrical energy;

taking first and second samples of said pulse of electrical energy to determine a rate of light decay within one of said first or said second scintillating crystals, said first and second samples taken during the integration time selected for said first scintillating crystal having said faster decay constant;

calculating the ratio of said first sampled pulse of electrical energy to said second sampled pulse of electrical energy to determine in which of said first or second scintillating crystals said gamma ray event occurred, said ratio being smaller for said second scintillating crystal than for said first scintillating crystal;

identifying in which of said first or second scintillating crystals said gamma ray event occurred;

stopping said integration process at said selected integration time for said first scintillating crystal having the faster decay constant if said gamma ray event is determined to have occurred in said first scintillating crystal;

continuing said integration process for said selected integration time for said second scintillating crystal if said gamma ray event is determined to have occurred in said second scintillating crystal, thereby acquiring a higher percentage of light.

16. The method of claim 15 wherein said tomography system is a positron emission tomography system.

17. The method of claim 16 wherein said photon converter used to accomplish said step of converting light generated by one of said first or second scintillating crystals into a pulse of electrical energy is a photomultiplier tube.

18. The method of claim 16 wherein said photon converter used to accomplish said step of converting light generated by one of said first or second scintillating crystals into a pulse of electrical energy is an avalanche photo diode.

19. The method of claim 16 wherein said step for beginning integration of said pulse of electrical energy includes the use of a gated integrator.

20. The method of claim 16 wherein said step for beginning integration of said pulse of electrical energy includes the use of a continuous sampling analog-to-digital converter and a digital summer/accumulator.

21. The method of claim 16 wherein said step of taking first and second samples of said pulse of electrical energy is accomplished by using an analog-to-digital converter.

22. The method of claim 16 wherein said first scintillating crystal is fabricated primarily from lutetium oxyorthosilicate, and said second scintillating crystal is fabricated primarily from sodium iodide.

23. The method of claim 16 wherein said first scintillating crystal is fabricated primarily from lutetium oxyorthosilicate, and said second scintillating crystal is fabricated primarily from bismuth germanium.

24. The method of claim 15 for reducing pile-up errors in a tomography system wherein said tomography system is a single photon emission computed tomography system.

25. An emission tomography system for reducing pile-up errors, the emission tomography system having a gurney for holding a patient, and the emission tomography system also having a plurality of detectors, comprising:

first scintillating crystals within said plurality of detectors for receiving gamma rays during tomography, said first scintillating crystals generating light upon receiving a gamma ray, with each of said first scintillating crystals having a decay constant, and wherein said first scintillating crystals are arranged in an array having a selected number of rows and columns within said plurality of detectors, second scintillating crystals within said plurality of detectors for receiving gamma rays during tomography, said second scintillating crystals generating light upon receiving a gamma ray, with said second scintillating crystals having a decay constant which is slower than said decay constant for said first scintillating crystals, and wherein each of said second scintillating crystals is associated with a corresponding first scintillating crystal in accordance with said first scintillating crystal array within said plurality of detectors;

a photon converter for converting light generated by one of said first and said second scintillating crystals into a pulse of electrical energy upon interaction with a gamma ray during tomography;

an integrator for beginning integration of said pulse of electrical energy;

sampling means for taking first and second samples of said pulse of electrical energy to determine the rate of light decay within one of said first and second scintillating crystals, said first and second samples taken during the integration time selected for said first scintillating crystals, said integration time being selected based upon a light decay time of said first scintillating crystals and a percentage of the total crystal light output required for tomography;

signal processing circuitry for calculating the ratio of said first to second sampled pulses of electrical energy to determine in which of said first or second scintillating crystals said gamma ray event occurred, said ratio being smaller if said gamma ray event occurred in one of said first scintillating crystals than in one of said second scintillating crystals;

signal processing circuitry for identifying in which of said first or second scintillating crystals said gamma ray event occurred;

signal processing circuitry for stopping said integration process at said selected integration time for said first scintillating crystals if one of said first scintillating crystals is identified; and signal processing circuitry for continuing said integration process during the integration time selected for said second scintillating crystals having the slower decay constant, said integration time being selected based upon a light decay time of said second scintillating crystals and a percentage of the total crystal light output that is needed for tomography, thereby acquiring a higher percentage of light if one of said second scintillating crystals is identified.

26. The emission tomography system of claim 25 wherein said tomography system is a positron emission tomography system.

27. The emission tomography system of claim 26 wherein said photon converter is a photomultiplier tube.

28. The emission tomography system of claim 26 wherein said photon converter is an avalanche photo diode.

29. The emission tomography system of claim 26 wherein said integrator includes a gated integrator.

30. The emission tomography system of claim 26 wherein said integrator includes a continuous sampling analog-to-digital converter and a digital summer/accumulator.

31. The emission tomography system of claim 26 wherein said sampling means for taking first and second samples of said pulse of electrical energy is an analogto-digital converter.

32. The emission tomography system of claim 26 wherein said first scintillating crystals are fabricated primarily from lutetium oxyorthosilicate, and said second scintillating crystals are fabricated primarily from sodium iodide.

33. The emission tomography system of claim 26 wherein said first scintillating crystals are fabricated primarily from bismuth germanium, and said second scintillating crystals are comprised primarily of sodium iodide.

34. The emission tomography system of claim 25 wherein said tomography system is a single photon emission computed tomography system.

* * * * *